United States Patent
Ferruti et al.

[11] Patent Number: 5,916,998
[45] Date of Patent: Jun. 29, 1999

[54] COPOLYMERS WITH POLYESTER POLYCARBONATE BLOCKS CONTAINING POLY(CAPROLACTONE) SEGMENTS, AND USE THEREOF FOR THE PREPARATION OF BIODEGRADABLE MATRICES

[75] Inventors: Paolo Ferruti, Milan; Maurizio Penco, Leghorn; Elisabetta Ranucci, Brescia, all of Italy

[73] Assignee: ASTA Medica Aktiengesellschaft, Dresden, Germany

[21] Appl. No.: 08/796,576

[22] Filed: Feb. 7, 1997

[30] Foreign Application Priority Data

Feb. 8, 1996 [IT] Italy .................................. MI96A0238

[51] Int. Cl.⁶ ................................................... C08G 64/00
[52] U.S. Cl. ............................................ 528/196; 525/461
[58] Field of Search ............................. 528/196; 525/461

[56] References Cited

FOREIGN PATENT DOCUMENTS 11441   5/1994   WIPO .
12629   5/1995   WIPO .

*Primary Examiner*—Terressa Mosley
*Attorney, Agent, or Firm*—Pillsbury Madison & Sutro LLP

[57] ABSTRACT

The invention relates to block copolymers of general formula (I)

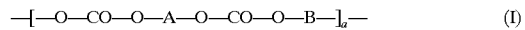

(I)

where a is an integer between 2 and 300 inclusive;

A and B, which may be the same or different, are blocks which can be obtained by reaction between a bis (chloroformate) of oligomeric poly(caprolactone) and a polyester residue of formula (II)

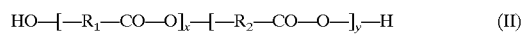

(II)

where $R_1$ and $R_2$, which may be the same or different, are each an aliphatic hydrocarbon residue with a linear or branched chain having from 1 to 4 carbon atoms; x and y are integers from 1 to 50, in any possible ratio from 0 to 1;

the groups —$R_1$—COO— and —$R_2$—COO— being randomly distributed in the polyester residue.

22 Claims, No Drawings

COPOLYMERS WITH POLYESTER POLYCARBONATE BLOCKS CONTAINING POLY(CAPROLACTONE) SEGMENTS, AND USE THEREOF FOR THE PREPARATION OF BIODEGRADABLE MATRICES

The present invention relates to block copolymers and to their use as biodegradable matrices for the controlled release of medicaments.

BACKGROUND OF THE INVENTION

In general, the polymers used as supports for controlled-release medicaments must be biocompatible, non-toxic and free of impurities. In particular, biodegradable polymers must give non-toxic, non-carcinogenic and non-teratogenic degradation products and must be readily eliminated.

The factors which influence the biodegradability are the particle sizes, morphology and chemical structure. Among these factors, the crystallinity has an important role, both from the point of view of the biodegradability and from the technological point of view of working of the polymers.

The common techniques of microencapsulation comprise coacervation, evaporation of the emulsified solvent and coextrusion. The latter is the preferred technique since it avoids the use of solvents and consequently poses no toxicological problems arising from residues thereof.

Extrudable polymers must be stable at the temperature of coextrusion, and must have a softening temperature which is not too high, to avoid decomposition of the medicament, but not too low either, to avoid problems of conservation.

Examples of pharmaceutical formulations in which the medicament (active principle) is incorporated in a biodegradable matrix are known in the literature. See for example "Biodegradable Polymers as Drug Delivery Systems", ed. by M. Chasin and R. Langer, Marcel Dekker Inc., New York 1990; "Methods in Enzymology, Vol. 112, Drug and Enzyme Targeting, Part A, ed. by K. J. Widder and R. Green, Academic Press. Inc., Orlando, Fla., 1985; "Formes Pharmaceutiques Nouvelles", P. Buri, F. Puisieux, E. Dalker, J. P. Benoît, Technique and Documentation (Lavoisier), Paris, 1985; "Biodegradable Polymers for controlled release of peptides and proteins", F. G. Hutchison and B. J. A. Furr, in Drug Carrier Systems, F. H. D. Roerdink and A. M. Kroom eds., John Wiley and Sons, Chichester, 1989; "Controlled Release of Biologically Active Agents" Richard Baker, John Wiley and Sons, New York, 1987.

Many types of polymers have been used for the above-mentioned purposes, and, among these, polycarbonates have demonstrated suitable biocompatiblity characteristics.

Kawaguchi et al. (Chem. Pharm. Bull. Vol. 31, n. 4, 1400–1403, 1983) describe the biodegradability of tablets made of polyethylene carbonate and polypropylene carbonate and the possibility of obtaining biocompatible materials of programmed degradation using suitable mixtures of the two polycarbonates.

Polycarbonates are polymers which have been known for a long time. Aliphatic polycarbonates are known, for example, from DE 2,546,534, published on Apr. 28, 1977, JP 6224190, published on Oct. 22, 1987 and JP 1009225, published on Jan. 12, 1989, these patents proposing them as plasticizers and intermediates for the preparation of polyurethanes (see also U.S. Pat. No. 4,105,641, granted on Aug. 8, 1978).

Polycarbonates of homo- and copolymeric nature have also been proposed. U.S. Pat. No. 4,716,203 (American Cyanamid), granted on Dec. 29, 1987, describes diblock and triblock copolymers having a first block of glycolic acid ester linked with trimethylene carbonate; triblock copolymers have an intermediate block obtained from ethylene oxide homopolymer or ethylene oxide/cyclic ether copolymer, or alternatively from macrocyclic ether copolymers. These copolymers are bioabsorbable and are indicated for the finishing of synthetic surgical threads.

International patent application WO 89/05664, in the name of Allied-Signal Inc., published on Jun. 29, 1989, describes medical devices formed partly or totally of polycarbonate homopolymers or copolymers which can contain polyether-polyamine portions in the polymer chain.

European patent application EP 0,427,185, in the name of Boehringer Ingelheim, published on Jan. 15, 1991, describes copolymers obtained from trimethylene carbonate and optically inactive lactides, which are useful for the manufacture of surgical grafts.

International patent applications WO 92/22600 and WO 95/12629, in the name of the Applicant, describe polyester polycarbonate random block copolymers which are useful as biodegradable matrices.

One problem which is posed in the use of biodegradable matrices is the biodegradation time of the material, which is usually too short.

The rate of degradation is a function of the hydrolytic susceptibility of the polyester blocks.

Another problem consists of the presence of crystallinity in the material. Indeed, biodegradable materials having a certain degree of crystallinity have markedly longer degradation times when compared with a completely amorphous analogous material. Therefore, the presence of a crystalline phase allows the development of products which are useful when long degradation times are required. Another appreciable effect of this factor is a substantial increase in the mechanical properties, for example the elastic modulus. This is potentially useful when a use as subcutaneous implants is envisaged. However, this crystallinity is lost when the material comes into contact with an aqueous medium or when it absorbs moisture.

Moreover, in the working of polymers by extrusion (one of the preferred methods), the melting range must be such as to be able to work the polymer easily without adversely affecting the active principle contained therein.

The preparation of block polyesters based on poly (caprolactone) and PLGA is described in the literature (C.A. 114: 229486y; C.A. 109: 190883e; C.A. 104: 89084s; C.A. 116: 21504w). These materials are prepared by one- or two-step copolymerization processes by means of ring opening of cyclic monomers.

These processes lead to systems which can only contain more than two or three blocks with difficulty. Moreover, the nature of the reaction and the method used do not allow full control of the structure of the product obtained. There are two fundamental reasons for this, which are well discussed in the publications cited. The first limiting factor consists of the diverse reactivity presented by various cyclic monomers (caprolactone, lactide and glycolide). This greatly limits the control of the length of the various blocks, and allows the production of diblock, or at the most triblock, systems. Another factor, which is by far more limiting, consists of the occurrence, during the polymerization reactions, of structure randomization phenomena; that is to say that as the conversion increases, the block structure converts into a random structure of statistical type.

SUMMARY OF THE INVENTION

It has now been found that polymerization by means of a chain-extension reaction between a bis-chloroformate of an oligomeric poly(caprolactone), prepared by reaction of phosgene with a hydroxy-terminal oligomeric poly(caprolactone), and a polyester oligomer of formula (II)

$$HO—[—R_1—CO—O—]_x—[—R_2—CO—O—]_y—H \qquad (II)$$

as defined below, allows the production of multiblock structures in which the various polyester segments are linked together by an ester bond and a carbonate bond.

As well as producing polymers having novel structures, the synthesis of these materials makes it possible to overcome a whole series of problems, as discussed above, presented by materials containing structures which are comparable but different in substance.

In particular, the reduced hydrophilic nature of these blocks limits the absorption of water by the material, thereby presumably also lowering the rate of hydrolytic degradation of the polyester blocks (II).

Advantageously, it is possible to obtain materials having a certain degree of crystallinity which remains even in aqueous medium.

The products obtained have a degree of crystallinity which can be modified depending on the type of poly(caprolactone) segment used.

A large increase in the biodegradation time of the material is therefore obtained. The reason for this is that the insertion of ε-hydroxy acid polyester blocks greatly decreases the susceptibility to hydrolysis of the material.

Moreover, the working range of the semi-crystalline products is similar to that of the previous products. The reason for this is that both PEG blocks and poly(caprolactone) blocks show melting points in the range 40–60° C., this being the optimum range for products used in extrusion processes.

DETAILED DESCRIPTION OF THE INVENTION

One subject of the present invention is block copolymers of general formula (I)

$$—[—O—CO—O—A—O—CO—O—B—]_a— \qquad (I)$$

where a is an integer between 2 and 300 inclusive;

A and B, which may be the same or different, are blocks which can be obtained by reaction between a bis(chloroformate) of oligomeric poly(caprolactone) and a polyester residue of formula (II)

$$HO—[—R_1—CO—O—]_x—[—R_2—CO—O—]_y—H \qquad (II)$$

where $R_1$ and $R_2$, which may be the same or different, are each an aliphatic hydrocarbon residue with a linear or branched chain having from 1 to 4 carbon atoms; x and y are integers from 1 to 50, in any possible ratio from 0 to 1; the groups —$R_1$—COO— and —$R_2$—COO— being randomly distributed in the polyester residue.

In a second embodiment, a subject of the present invention is block copolymers of formula (I)

$$—[—O—CO—O—A—O—CO—O—B—]_a— \qquad (I)$$

where:

a is an integer between 2 and 300 inclusive;

A and B, which may be the same or different, are polyester blocks of formula (III)

$$—[—R_1—CO—O—]_x—[—R_2—CO—O—]_y—R_3— \qquad (III)$$

where:

$R_1$ and $R_2$, which may be the same or different, are an aliphatic hydrocarbon residue with a linear or branched chain having from 1 to 4 carbon atoms, x and y are integers from 1 to 50, in any possible ratio from 0 to 1, the groups —$R_1$—COO— and —$R_2$—COO— being randomly distributed in the polyester residue;

$R_3$ is a residue of formula (IV)

$$—(—[CH_2]_5—COO—)_m—R_4— \qquad (IV)$$

m is an integer between 1 and 200, preferably between 2 and 100, where $R_4$ is an aliphatic hydrocarbon residue with a linear or branched chain having from 2 to 18 carbon atoms; or a cycloaliphatic hydrocarbon residue having from 3 to 8 carbon atoms optionally bearing one or more linear or branched alkyl substituents having from 1 to 4 carbon atoms;

or alternatively $R_3$ is a residue of formula (V)

$$—(—[CH_2]_5—COO—)_m—R_4—(—OCO—[—CH_2—]_5—)_{m_1}— \qquad (V)$$

where $R_4$ is defined as above, and m and $m_1$, which may be the same or different, are an integer between 1 and 200.

The expression aliphatic hydrocarbon residue with a linear or branched chain having from 1 to 4 carbon atoms is understood to refer, for example, to:

—$CH_2$—; —$CH_2$—$CH_2$—; —$(CH_2)_3$—; —$(CH_2)_4$—; —$CH(CH_3)$—;

—$CH(CH_3)$—$CH_2$—; —$CH(C_2H_5)$—.

The expression aliphatic hydrocarbon residue with a linear or branched chain having from 2 to 18 carbon atoms is understood to refer, for example, to:

—$(CH_2)_2$—; —$(CH_2)_4$—; —$(CH_2)_8$—; —$(CH_2)_{10}$—; —$(CH_2)_{14}$—;

—$CH(CH_3)$—$(CH_2)_{16}$.

The expression cycloaliphatic hydrocarbon residue having from 3 to 8 carbon atoms is understood to refer, for example, to cyclopropyl, cyclobutyl, cyclopentyl, cyclohexyl and cyclooctyl. Examples of optional linear or branched alkyl substituents are methyl, ethyl, isopropyl, sec-butyl and tert-butyl.

A first group of preferred polymers are those in which, in the polyester blocks (II) and (III), $R_1$ and $R_2$ are —$(CH_2)$— and —$CH(CH_3)$— residues, that is to say that the polyester blocks consist of lactic acid/glycolic acid, in particular in a 1:1 molar ratio.

A second group of preferred polymers are those with number-average molecular weights of between 10,000 and 400,000.

A third group of preferred polymers are those with number-average molecular weights of between 25,000 and 67,000, in particular those of weight 67,400, 48,100, 33,200, 51,400, 49,700, 27,600 and 63,800.

The polymers of the present invention may be obtained by a chain-extension reaction between a bis(chloroformate) of an oligomeric poly(caprolactone) with a polyester residue of formula (II) as described above.

The polyester block is prepared by reaction under vacuum of a mixture of hydroxy acids of formulae (VI) and (VII)

$$\text{HO}-\text{R}_1-\overset{\overset{\displaystyle O}{\|}}{\text{C}}-\text{OH} \quad \text{and} \quad \text{HO}-\text{R}_2-\overset{\overset{\displaystyle O}{\|}}{\text{C}}-\text{OH}$$

$$\text{(VI)} \quad\quad\quad\quad \text{(VII)}$$

where $R_1$ and $R_2$ are as defined above, to give the polyester oligomer (II)

$$\text{HO}\mathrm{-\!\!\!\!-}[\mathrm{-R_1-CO-O}]_x\mathrm{-\!\!\!\!-}[\mathrm{-R_2-CO-O-}]_y\mathrm{-H} \qquad \text{(II)}$$

where $R_1$, $R_2$, x and y are as defined above.

The starting materials are normally commercially available and are, in any case, described in the chemical literature.

The formulation of the polyester (II) takes place under at atmosphere of inert gas, for example nitrogen or argon, at a temperature of 170–220° C., preferably 180–200° C., for a period of 15–30 hours, preferably 20–25 hours. This stage is followed by a stage of reaction under a vacuum of 5–0.001 mmHg, preferably less than 1 mmHg, for the same period of time and at the same temperature.

After the stage under vacuum, the oligomer is cooled, while still maintaining the vacuum, and is isolated by precipitation from chloroform/ethyl ether.

The polyester (II) is then reacted with the poly(caprolactone) bis(chloroformate) of formula (VIII)

$$\text{Cl}-\overset{\overset{\displaystyle O}{\|}}{\text{C}}-\text{O}-\text{R}_3-\text{O}-\overset{\overset{\displaystyle O}{\|}}{\text{C}}-\text{Cl} \qquad \text{(VIII)}$$

where $R_3$ is as in formula (I), in a chlorinated solvent, optionally in the presence of a tertiary amine, at a temperature between −10 and 50° C., preferably 0–30° C., followed by application of the vacuum (pressure of 5–0.001 mmHg, preferably 1–0.01 mmHg), for a period of time between 4 and 30 hours, preferably between 15 and 20 hours.

In particular, according to the present invention, a process is provided in which a diol of formula (IX)

$$\text{HO}-\text{R}_3-\text{OH} \qquad \text{(IX)}$$

where $R_3$ is as defined above, is reacted with phosgene to give the corresponding bis(chloroformate), which product is reacted with a polyester oligomer of formula (II) optionally in the presence of one or more tertiary amines, followed by a stage at reduced pressure, to give the copolymer of formula (I).

The bis(chloroformate) is prepared by reaction between a hydroxy-terminal poly(caprolactone) of formula (IVa) or (Va)

$$\text{HO}-(-[\text{CH}_2]_5-\text{COO}-)_m-\text{R}_4-\text{OH} \qquad \text{(IVa)}$$

$$\text{HO}-(-[\text{CH}_2]_5-\text{COO}-)_m-\text{R}_4-(-\text{OCO}-[-\text{CH}_2]_5)_{m1}-\text{OH} \qquad \text{(Va)}$$

where m and $m_1$ are as defined above, and phosgene. The procedure and the reaction conditions are known to those skilled in the art and are, in any case, described in the literature.

Hydroxy-terminal poly(caprolactones) of the type described by formula (IVa) are commercially available. Alternatively, they may be prepared by a reaction of poly(caprolactone) with an excess of diol HO—$R_4$—OH.

In a different embodiment, the hydroxy-terminal poly(caprolactone) of formula (Va) is obtained according to procedures described in the chemical literature, for example in U.S. Pat. No. 3,654,347 and DE 2,634,211.

When there is no advantage in having particularly high molecular weights, it is convenient to react the polyester oligomer (II) with phosgene to give the chloroformate (XI)

$$\text{Cl}-\text{CO}(\text{O}-\text{R}_1-\overset{\overset{\displaystyle O}{\|}}{\text{C}})_{\!\!x}(\text{O}-\text{R}_2-\overset{\overset{\displaystyle O}{\|}}{\text{C}})_{\!\!y}\text{Cl} \qquad \text{(XI)}$$

which is then reacted with a diol of formula (X)

$$\text{HO}-\text{R}_3-\text{OH} \qquad \text{(X)}$$

to give a copolymer of formula (I).

The polymers which form the subject of the invention have advantageous physicochemical properties which make them suitable for use as biodegradable matrices. In particular, these polymers are of modifiable crystallinity and this property imparts good characteristics of biodegradability and of workability thereto, in particular in the coextrusion technique.

Thus, another subject of the invention is the use of the polymers described above for the preparation of biodegradable matrices, and the matrices thus obtained.

The matrices are preferably prepared by coextrusion of a mixture of the active principle under consideration and the polymer which constitutes the matrix. Several polymers may also be used. The matrix may also contain conventional additives.

If desired, the matrices according to the present invention can also be prepared by other methods known to those skilled in the art.

In another of its aspects, the present invention provides pharmaceutical compositions with controlled release of the active principle, comprising a biodegradable matrix as described above, optionally mixed with conventional excipients and vehicles.

The present invention finds an advantageous application in the production of controlled-release pharmaceutical compositions, for example as subcutaneous implants, and in the production of physiologically active peptides, for example those described in EP 0,531,461 and EP 0,593,491.

The examples which follow further illustrate the invention.

EXAMPLE 1

243.33 g of an aqueous 72% by weight solution of D,L-lactic acid and 151.15 g of 99% glycolic acid were placed in a three-necked, round-bottomed flask fitted with a Dean-Stark system and under a nitrogen atmosphere. The mixture was maintained under a stream of nitrogen and with stirring at a temperature of 200° C. for 24 hours. A vacuum (<1 mmHg) was then applied for 24 hours at the same temperature.

After cooling under vacuum, dissolution in chloroform (2 ml of chloroform per gram of polymer) and precipitation in ethyl ether, 267 g of oligomer were obtained with a number-average molecular weight of 1,890 (evaluated by titration in benzyl alcohol with a standard 0.1 N solution of tetrabutylammonium hydroxide in isopropanol) and an intrinsic viscosity of 0.106 dl/g, measured in chloroform at a temperature of 32° C.

EXAMPLE 2

In a manner similar to that described in Example 1, 243.33 g of a 72% by weight solution of D,L-lactic acid and 50.38 g of 99% by weight glycolic acid were reacted together. 170 g of oligomer were thus obtained having a number-average molecular weight of 2,540 (evaluated by titration in benzyl alcohol with a standard 0.1 N solution of tetrabutylammonium hydroxide in isopropanol) and an intrinsic viscosity of 0.126 dl/g, measured in chloroform at a temperature of 32° C.

EXAMPLE 3

In a manner similar to that described in Example 1, 243.33 g of a 72% by weight solution of D,L-lactic acid were reacted together. 125 g of oligomer were thus obtained having a number-average molecular weight of 2,630 (evaluated by titration in benzyl alcohol with a standard 0.1 N solution of tetrabutylammonium hydroxide in isopropanol) and an intrinsic viscosity of 0.132 dl/g, measured in chloroform at a temperature of 32° C.

EXAMPLE 4

In a manner similar to that described in Example 1, 243.3 g of a 72% by weight solution of D,L-lactic acid and 151.15 g of 99% by weight glycolic acid were reacted together. 220 g of oligomer were thus obtained having a number-average molecular weight of 1,540 (evaluated by titration in benzyl alcohol with a standard 0.1 N solution of tetrabutylammonium hydroxide in isopropanol) and an intrinsic viscosity of 0.096 dl/g, measured in chloroform at a temperature of 32° C.

EXAMPLE 5

In a manner similar to that described in Example 1, 243.33 g of an 80% by weight solution of L-lactic acid were reacted together. 130 g of oligomer were thus obtained having a number-average molecular weight of 3,020 (evaluated by titration in benzyl alcohol with a standard 0.1 N solution of tetrabutylammonium hydroxide in isopropanol) and an intrinsic viscosity of 0.143 dl/g, measured in chloroform at a temperature of 32° C.

EXAMPLE 6

22 ml of a solution of phosgene in toluene (1.93 M titer) was introduced into a three-necked round-bottomed flask fitted with a dropping funnel, under an atmosphere of anhydrous nitrogen. After cooling 0° C., a solution containing 20 g of polycaprolactone oligomer diol 1250, 36 ml of chloroform and 5.74 ml of N-ethyl-diisopropylamine were added dropwise. After 20 minutes, the excess phosgene was removed by flushing with nitrogen. A solution composed of 30 g of 1:1 PLGA (oligomer described in Example 1), 55 ml of chloroform, 5.74 ml of N-ethyldiisopropylamine and 2.02 g of 4-dimethylaminopiridine was then added dropwise. The mixture was maintained at 0° C. for 4 hours and then warmed to room temperature and maintained at that temperature for 12 hours. The mixture was concentrated for 4 hours under vacuum (<1 mmHg), taken up in chloroform and precipitated from heptane. After reprecipitation and extraction with ether, 48 g of polymer were obtained having a number-average molecular weight of 67,400, an intrinsic viscosity of 1, 198 dl/g, glass transition temperatures of 61° C. and 30° C. respectively and a melting point of 59° C.

A sample of copolymer in the form of microspheres with an average diameter of 50 μm gave a dissolution time of 3 months. By comparison, identical microspheres consisting of a 75:25 PLGA copolymer (number-average molecular weight of 50,000), described in WO 95/12629, gave a dissolution time of 2 months.

EXAMPLE 7

Using a procedure similar to that described in Example 7, 30 g of PLGA oligomer (described in Example 1) and 32 g of polycaprolactone diol oligomer having a number-average molecular weight of 2,000 were reacted together. 60 g of polymer were thus obtained having a number-average molecular weight of 48,100, an intrinsic viscosity of 0.823 dl/g, glass transition temperatures of −61° C. and 28° C. and a melting point of 60° C.

EXAMPLE 8

Using a procedure similar to that described in Example 7, 30 g of PLGA oligomer (described in Example 1) and 8.48 g of polycaprolactone diol oligomer having a number-average molecular weight of 530 were reacted together. 35 g of polymer were thus obtained having a number-average molecular weight of 33,200, an intrinsic viscosity of 0.765 dl/g, and a glass transition temperature of 38° C.

EXAMPLE 9

Using a procedure similar to that described in Example 7, 40.64 g of PLGA oligomer (described in Example 2) and 8.48 g of polycaprolactone diol oligomer having a number-average molecular weight of 530 were reacted together. 45 g of polymer were thus obtained having a number-average molecular weight of 51,400, an intrinsic viscosity of 0.967 dl/g, and a glass transition temperature of 42° C.

EXAMPLE 10

Using a procedure similar to that described in Example 7, 42.1 g of PLGA oligomer (described in Example 3) and 8.48 g of polycaprolactone diol oligomer having a number-average molecular weight of 530 were reacted together. 47 g of polymer were thus obtained having a number-average molecular weight of 49,700, and an intrinsic viscosity of 0.887 dl/g.

EXAMPLE 11

Using a procedure similar to that described in Example 7, 24.6 g of PLGA oligomer (described in Example 4) and 8.48 g of polycaprolactone diol oligomer having a number-average molecular weight of 530 were reacted together. 29 g of polymer were thus obtained having a number-average molecular weight of 27,600, and an intrinsic viscosity of 0.561 dl/g.

EXAMPLE 12

Using a procedure similar to that described in Example 7, 48.3 g of PLGA oligomer (described in Example 5) and 8.48 g of polycaprolactone diol oligomer having a number-average molecular weight of 530 were reacted together 53 g of polymer were thus obtained having a number-average molecular weight of 63,800, and an intrinsic viscosity of 1.012 dl/g.

We claim:

1. Block copolymers of general formula (I)

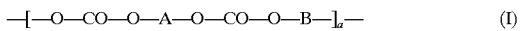

where a is an integer between 2 and 300 inclusive;

A and B, which are the same or different, are blocks which can be obtained by reaction between a bis (chloroformate) of oligomeric poly(caprolactone) and a polyester residue of formula (II)

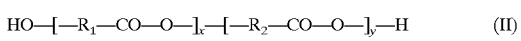

where $R_1$ and $R_2$, which are the same or different, are each an aliphatic hydrocarbon residue with a linear or branched chain having from 1 to 4 carbon atoms; x and y are integers from 1 to 50, in a ratio from 0 to 1;

the groups —$R_1$—COO— and —$R_2$—COO— being randomly distributed in the polyester residue.

2. Copolymers according to claim 1, in which the polyester residue is a lactic acid/glycolic acid polyester; x and y are as defined above.

3. Copolymers according to claim 2, in which the polyester residue is a lactic acid/glycolic acid polyester in a 1:1 molar ratio.

4. Block copolymers of formula (I)

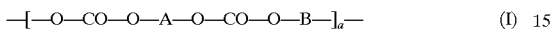  (I)

where:

a is an integer between 2 and 300 inclusive;

A and B, which are the same or different, are polyester blocks of formula (III)

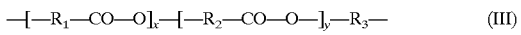  (III)

where:

$R_1$ and $R_2$, which are the same or different, are an aliphatic hydrocarbon residue with a linear or branched chain having from 1 to 4 carbon atoms, x and y are integers from 1 to 50, in a ratio from 0 to 1, the groups —$R_1$—COO— and —$R_2$—COO— being randomly distributed in the polyester residue;

$R_3$ is a residue of formula (IV)

  (IV)

m is an integer between 1 and 200, where $R_4$ is an aliphatic hydrocarbon residue with a linear or branched chain having from 2 to 18 carbon atoms; or a cycloaliphatic hydrocarbon residue having from 3 to 8 carbon atoms optionally bearing one or more linear or branched alkyl substituents;

or alternatively $R_3$ is a residue of formula (V)

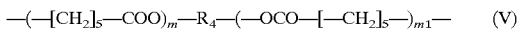  (V)

where $R_4$ is defined as above, and m and $m_1$, which are the same or different, are an integer between 1 and 200.

5. Copolymers according to claim 4, in which the polyester block of formula (III) is a lactic acid/glycolic acid polyester; x, y and $R_3$ are as defined above.

6. Copolymers according to claim 5, in which the polyester block of formula (III) consists of a lactic acid/glycolic acid polyester in a 1:1 molar ratio.

7. Copolymer according to claim 1 or 4, having a number-average molecular weight of 67,400 measured by size exclusion chromatography.

8. Copolymer according to claim 1 or 4, having a number-average molecular weight of 48,100 measured by size exclusion chromatography.

9. Copolymer according to claim 1 or 4, having a number-average molecular weight of 33,200 measured by size exclusion chromatography.

10. Copolymer according to claim 1 or 4, having a number-average molecular weight of 51,400 measured by size exclusion chromatography.

11. Copolymer according to claim 1 or 4, having a number-average molecular weight of 49,700 measured by size exclusion chromatography.

12. Copolymer according to claim 1 or 4, having a number-average molecular weight of 27,600 measured by size exclusion chromatography.

13. Copolymer according to claim 1 or 4, having a number-average molecular weight of 63,800 measured by size exclusion chromatography.

14. Process for the preparation of copolymers of claim 4, which process comprises the following stages:

a) Reaction under vacuum of a mixture of hydroxy acids of formulae (VI) and (VII)

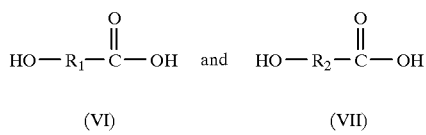

(VI)　　　　(VII)

where $R_1$ and $R_2$ are as defined above, to give the polyester oligomer (II)

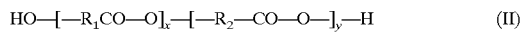  (II)

where $R_1$, $R_2$, x and y are as defined above;

b) The polyester (II) is then reacted with the bis(chloroformate) of formula (VIII)

(VIII)

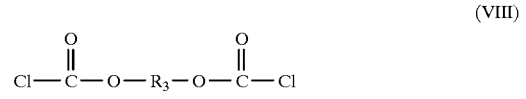

in which $R_3$ is as in formula (I), optionally in the presence of one or more tertiary amines, followed by a stage at reduced pressure.

15. Process for the preparation of copolymers of claim 4, in which a diol of formula (IX)

HO—$R_3$—OH　　　　(IX)

where $R_3$ is as defined above, is reacted with phosgene to give the corresponding bis(chloroformate), which product is reacted with a polyester oligomer of formula (II) optionally in the presence of one or more tertiary amines, followed by a stage at reduced pressure, to give the copolymer of formula (I).

16. Process for the preparation of copolymers of claim 4, which comprises the reaction of a hydroxy-terminal poly(caprolactone) of formula (IVa)

  (IVa)

where $R_4$ and m are as defined above, with phosgene, followed by reaction with a polyester of formula (II)

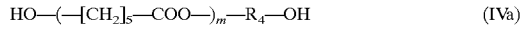  (II)

where $R_1$, $R_2$, x and y are as defined above, optionally in the presence of one or more tertiary amines, followed by a stage at reduced pressure.

17. Process for the preparation of copolymers of claim 4, which comprises the reaction of a hydroxy-terminal poly(caprolactone) of formula (Va)

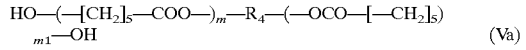  (Va)

where $R_4$, m and $m_1$ are as defined above, with phosgene, followed by reaction with a polyester of formula (II)

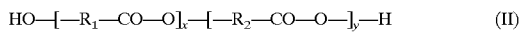 (II)

where $R_1$, $R_2$, x and y are as defined above, optionally in the presence of one or more tertiary amines, followed by a stage at reduced pressure.

18. Process for the preparation of copolymers of claim 4, in which the polyester oligomer (II) is reacted with phosgene to give the chloroformate (XI)

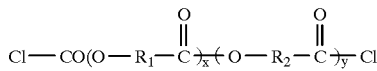 (XI)

which is then reacted with a diol of formula (X)

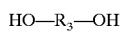 (X)

to give a copolymer of formula (I).

19. Biodegradable matrices comprising at least one copolymer of claims 1 or 4, optionally mixed with conventional additives.

20. Pharmaceutical composition with controlled release of the active principle, comprising a matrix of claim 19, optionally mixed with conventional excipients and vehicles.

21. A method of preparing a biodegradable matrix comprising combining an active principle and a copolymer of claim 1.

22. A method of preparing a biodegradable matrix comprising combining an active principle and a copolymer of claim 4.

* * * * *